(12) United States Patent
Kuppurathanam et al.

(10) Patent No.: US 8,834,552 B2
(45) Date of Patent: Sep. 16, 2014

(54) STENT GRAFT HAVING FLOATING YARNS

(75) Inventors: Shyam Sv Kuppurathanam, Bloomington, IN (US); Michael P. DeBruyne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 631 days.

(21) Appl. No.: 12/343,316

(22) Filed: Dec. 23, 2008

(65) Prior Publication Data

US 2009/0171443 A1    Jul. 2, 2009

Related U.S. Application Data

(60) Provisional application No. 61/016,993, filed on Dec. 27, 2007.

(51) Int. Cl.
*A61F 2/06* (2013.01)
*D03C 19/00* (2006.01)
*D03D 49/00* (2006.01)
*D03J 1/00* (2006.01)
*D03D 3/00* (2006.01)
*D03D 3/02* (2006.01)
*D03D 11/02* (2006.01)
*D03D 15/00* (2006.01)
*D03D 25/00* (2006.01)
*A61F 2/89* (2013.01)
*D03D 49/06* (2006.01)
*A61F 2/07* (2013.01)
*D03D 1/00* (2006.01)
*A61F 2/848* (2013.01)

(52) U.S. Cl.
CPC .......... *A61F 2/07* (2013.01); *D03D 2700/0174* (2013.01); *D03D 15/00* (2013.01); *D03D 49/06* (2013.01); *A61F 2002/075* (2013.01); *D03D 2700/02* (2013.01); *D03D 1/00* (2013.01); *A61F 2/89* (2013.01); *A61F 2/848* (2013.01); *D03D 3/02* (2013.01); *A61F 2002/065* (2013.01)
USPC ......... 623/1.13; 139/24; 139/321; 139/420 R; 139/387 R (58) Field of Classification Search
CPC .................................. A61F 2/07; A03D 15/00
USPC ........................ 139/420 R, 24, 321; 623/1.13
See application file for complete search history.

(56) References Cited

U.S. PATENT DOCUMENTS

| | | | |
|---|---|---|---|
| 2,677,397 A * | 5/1954 | Pfeiffer | 139/417 |
| 3,095,017 A | 6/1963 | Bleiler et al. | |
| 3,108,357 A | 10/1963 | Liebig | |
| 3,304,557 A * | 2/1967 | Seymour Polansky | 623/1.38 |
| 3,582,444 A | 6/1971 | Ngo et al. | |

(Continued)

*Primary Examiner* — David Isabella
*Assistant Examiner* — Jacqueline Woznicki
(74) *Attorney, Agent, or Firm* — Brinks Gilson & Lione (57) ABSTRACT

An implantable graft device is disclosed. The device comprises a graft body forming a lumen defining a longitudinal axis and comprising proximal and distal ends. The graft body comprises a woven fabric having warp yarns aligned in a first direction and weft yarns aligned in a second direction. The weft yarns are woven with the warp yarns. A portion of the warp yarns along the longitudinal axis of the graft body are not interwoven with the weft yarns, defining floating yarns having loops aligned in one of the first direction and the second direction. The device further comprises an expandable stent disposed circumferentially about the longitudinal axis and received through the loops of the floating yarns to attach the stent to the graft body.

17 Claims, 7 Drawing Sheets

(56) References Cited

U.S. PATENT DOCUMENTS

| | | | |
|---|---|---|---|
| 4,340,091 A | 7/1982 | Skelton et al. |
| 4,517,687 A | 5/1985 | Liebig et al. |
| 4,530,113 A | 7/1985 | Matterson |
| 4,610,688 A | 9/1986 | Silvestrini et al. |
| 4,652,263 A | 3/1987 | Herweck et al. |
| 4,670,286 A | 6/1987 | Nyilas et al. |
| 4,792,336 A | 12/1988 | Hlavacek et al. |
| 4,816,028 A | 3/1989 | Kapadia et al. |
| 4,834,755 A | 5/1989 | Silvestrini et al. |
| 4,892,539 A | 1/1990 | Koch |
| 5,127,919 A * | 7/1992 | Ibrahim et al. ............. 623/1.51 |
| 5,141,031 A * | 8/1992 | Baurmeister ............. 139/383 R |
| 5,178,630 A | 1/1993 | Schmitt |
| 5,197,977 A | 3/1993 | Hoffman, Jr. et al. |
| 5,217,493 A | 6/1993 | Raad et al. |
| 5,244,718 A * | 9/1993 | Taylor et al. ............. 442/208 |
| 5,282,848 A | 2/1994 | Schmitt |
| 5,366,504 A | 11/1994 | Andersen et al. |
| 5,370,682 A | 12/1994 | Schmitt |
| 5,385,580 A | 1/1995 | Schmitt |
| 5,487,858 A | 1/1996 | Schmitt |
| 5,496,364 A | 3/1996 | Schmitt |
| 5,509,931 A | 4/1996 | Schmitt |
| 5,599,321 A | 2/1997 | Conway et al. |
| 5,653,746 A | 8/1997 | Schmitt |
| 5,674,276 A | 10/1997 | Andersen et al. |
| 5,697,970 A | 12/1997 | Schmitt et al. |
| 5,733,327 A | 3/1998 | Igaki et al. |
| 5,800,514 A * | 9/1998 | Nunez et al. ............. 623/1.51 |
| 5,824,037 A * | 10/1998 | Fogarty et al. ............. 623/1.13 |
| 5,843,158 A | 12/1998 | Lenker et al. |
| 5,891,191 A | 4/1999 | Stinson |
| 5,904,714 A * | 5/1999 | Nunez et al. ............. 139/383 R |
| 5,976,179 A | 11/1999 | Inoue |
| 6,000,442 A * | 12/1999 | Busgen ............. 139/389 |
| 6,045,568 A | 4/2000 | Igaki et al. |
| 6,080,177 A | 6/2000 | Igaki et al. |
| 6,136,022 A | 10/2000 | Nunez et al. |
| 6,159,239 A * | 12/2000 | Greenhalgh ............. 623/1.13 |
| 6,161,399 A | 12/2000 | Jayaraman |
| 6,164,339 A | 12/2000 | Greenhalgh |
| 6,200,335 B1 | 3/2001 | Igaki |
| 6,221,099 B1 | 4/2001 | Andersen et al. |
| 6,346,492 B1 | 2/2002 | Koyfman |
| 6,387,122 B1 | 5/2002 | Cragg |
| 6,395,021 B1 | 5/2002 | Hart et al. |
| 6,485,524 B2 | 11/2002 | Strecker |
| 6,494,907 B1 | 12/2002 | Bulver |
| 6,540,773 B2 | 4/2003 | Dong |
| 6,547,820 B1 | 4/2003 | Staudenmeier |
| 6,581,366 B1 | 6/2003 | Andrews |
| 6,663,667 B2 | 12/2003 | Dehdashtian |
| 6,685,736 B1 | 2/2004 | White et al. |
| 6,792,979 B2 | 9/2004 | Konya et al. |
| 6,805,706 B2 | 10/2004 | Solovay et al. |
| 6,814,754 B2 | 11/2004 | Greenhalgh |
| 6,849,088 B2 | 2/2005 | Dehdashtian et al. |
| 6,881,221 B2 | 4/2005 | Golds |
| 7,063,721 B2 | 6/2006 | Takahashi et al. |
| 7,122,052 B2 | 10/2006 | Greenhalgh |
| 7,185,597 B1 | 3/2007 | Phillips et al. |
| 7,338,531 B2 | 3/2008 | Ellis et al. |
| 7,424,899 B2 * | 9/2008 | Mouri et al. ............. 139/384 R |
| 7,530,996 B2 | 5/2009 | Bentele et al. |
| 7,651,522 B2 | 1/2010 | Busch et al. |
| 7,670,367 B1 | 3/2010 | Chouinard et al. |
| 7,699,887 B2 | 4/2010 | Burnside et al. |
| 2001/0047198 A1 | 11/2001 | Drasler et al. |
| 2001/0056299 A1 | 12/2001 | Thompson |
| 2002/0034902 A1 | 3/2002 | Litton |
| 2002/0042644 A1 | 4/2002 | Greenhalgh |
| 2002/0052649 A1 | 5/2002 | Greenhalgh |
| 2002/0156522 A1 | 10/2002 | Ivancev et al. |
| 2003/0181970 A1 * | 9/2003 | Takahashi et al. ............. 623/1.13 |
| 2003/0181971 A1 * | 9/2003 | Takahashi et al. ............. 623/1.13 |
| 2003/0204235 A1 | 10/2003 | Edens et al. |
| 2003/0229389 A1 | 12/2003 | Escano |
| 2004/0209538 A1 | 10/2004 | Klinge et al. |
| 2004/0215320 A1 | 10/2004 | Machek |
| 2005/0008763 A1 | 1/2005 | Schachter |
| 2005/0149173 A1 | 7/2005 | Hunter et al. |
| 2005/0154444 A1 | 7/2005 | Quadri |
| 2005/0154446 A1 | 7/2005 | Phillips et al. |
| 2005/0163954 A1 | 7/2005 | Shaw |
| 2005/0187604 A1 | 8/2005 | Eells et al. |
| 2005/0240261 A1 | 10/2005 | Rakos et al. |
| 2005/0283224 A1 | 12/2005 | King |
| 2005/0288797 A1 | 12/2005 | Howland |
| 2006/0009835 A1 | 1/2006 | Osborne et al. |
| 2006/0019561 A1 | 1/2006 | Schindzielorz et al. |
| 2006/0020328 A1 | 1/2006 | Tan |
| 2006/0024496 A1 | 2/2006 | Hietpas et al. |
| 2006/0095119 A1 * | 5/2006 | Bolduc ............. 623/1.36 |
| 2006/0142840 A1 | 6/2006 | Sherry et al. |
| 2006/0293749 A1 | 12/2006 | Hudgins et al. |
| 2007/0207186 A1 | 9/2007 | Scanlon et al. |
| 2007/0224238 A1 | 9/2007 | Mansmann et al. |
| 2007/0270742 A1 | 11/2007 | Guetty |
| 2008/0228028 A1 * | 9/2008 | Carlson et al. ............. 600/36 |
| 2009/0171435 A1 * | 7/2009 | Kuppurathanam et al. .. 623/1.12 |
| 2009/0171451 A1 * | 7/2009 | Kuppurathanam et al. .. 623/1.36 |
| 2009/0192597 A1 | 7/2009 | Bentele et al. |
| 2009/0264925 A1 | 10/2009 | Hotter et al. |
| 2009/0264934 A1 | 10/2009 | Youssef et al. |
| 2009/0299408 A1 | 12/2009 | Schuldt-Hempe et al. |
| 2010/0063576 A1 * | 3/2010 | Schaeffer et al. ............. 623/1.13 |
| 2010/0074934 A1 | 3/2010 | Hunter |
| 2012/0168022 A1 * | 7/2012 | Rasmussen et al. ............. 139/11 |
| 2012/0171917 A1 * | 7/2012 | Rasmussen et al. ............. 442/199 |

* cited by examiner

STENT GRAFT HAVING FLOATING YARNS

CROSS-REFERENCE TO RELATED APPLICATIONS

This application claims the benefit of U.S. Provisional Application Ser. No. 61/016,993, filed on Dec. 27, 2007, entitled "STENT GRAFT HAVING FLOATING YARNS," the entire contents of which are incorporated herein by reference.

BACKGROUND OF THE INVENTION

The present invention relates generally to an improved vascular graft and method for bridging a defect in a main vessel near one or more branch vessels.

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

Although adequate, current processes of making and packaging a stent graft is relatively time consuming. For example, attaching a stent or wire about a graft body is relatively time consuming. This requires attachment processes such as suturing or sewing the stent to the graft, consuming a considerable amount of time to complete. Moreover, many stent graft manufacturers are challenged with the need to reduce the profile to facilitate an easier packagability of the stent graft.

BRIEF SUMMARY OF THE INVENTION

Embodiments of the present invention provide an improved stent graft device having floating yarns and methods of making the stent graft. The method of making the stent graft is relatively less time consuming and no holes are made through the graft body when attaching the stent to the graft body, thereby increasing the time efficiency to manufacture the device.

In one embodiment, the present invention provides an implantable graft device. The device comprises a graft body forming a lumen defining a longitudinal axis and comprising proximal and distal ends. The graft body comprises a woven fabric having warp yarns aligned in a first direction and weft yarns aligned in a second direction. The weft yarns are interwoven with the warp yarns. A portion of warp yarns along the longitudinal axis of the graft body are not interwoven with the weft yarns to define floating yarns having loops aligned in one of the first direction and second direction. The device further comprises an expandable stent disposed circumferentially about the longitudinal axis and received through the loops of the floating yarns to attach the stent to the graft body.

In another embodiment, the device further comprises an anchor portion extending from the proximal end of the graft body. The anchor portion has a first woven portion and a barb stent attached thereto for reduced migration of the graft device. The first woven portion is comprised of woven yarn. The device further comprises an end portion extending from the distal end of the graft body. The end portion has a second woven portion and a stent attached thereto. The second woven portion being comprised of woven yarn.

In another example, the present invention provides a method for making an implantable graft device. The method comprises forming a graft body having a lumen to define a longitudinal axis and comprising proximal and distal ends to define a woven fabric having warp yarns aligned in a first direction and weft yarns aligned in a second direction and interwoven with the warp yarns. A portion of the graft body has weft yarns that are not interwoven with the warp yarns, defining floating yarns aligned in the first direction circumferentially about the longitudinal axis. The method further comprises disposing a first end of an expandable stent circumferentially about the longitudinal axis and received through the floating yarns to attach the stent to the graft body. The method further comprises attaching a second end of the stent to the first end to close the stent about the graft body.

Further objects, features, and advantages of the present invention will become apparent from consideration of the following description and the appended claims when taken in connection with the accompanying drawings.

BRIEF DESCRIPTION OF THE DRAWINGS

FIG. 1b is an enlarged view of the implantable graft device in circle 1b of FIG. 1a;

FIG. 1c is a partial view of the graft device of FIG. 1a;

FIG. 1d is a plan view of a stent of the graft device of FIG. 1a;

FIG. 2 is an environmental view of the implantable graft device of FIG. 1a;

DETAILED DESCRIPTION OF THE INVENTION

The present invention provides for an implantable stent graft device with a graft body having floating yarns. The floating yarns are loops created by non-woven warp yarns to receive a stent circumferentially about the graft body. The loops receive the stent to attach the stent to the graft body, thereby increasing the time efficiency in manufacturing the stent graft device. Additionally, no holes are made through the graft body in attaching the stent thereto.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, biliary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis.

The term "stent graft" as used herein refers to a prosthesis comprising a stent and a graft material associated therewith that forms a lumen through at least a portion of its length.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Figure 1A:
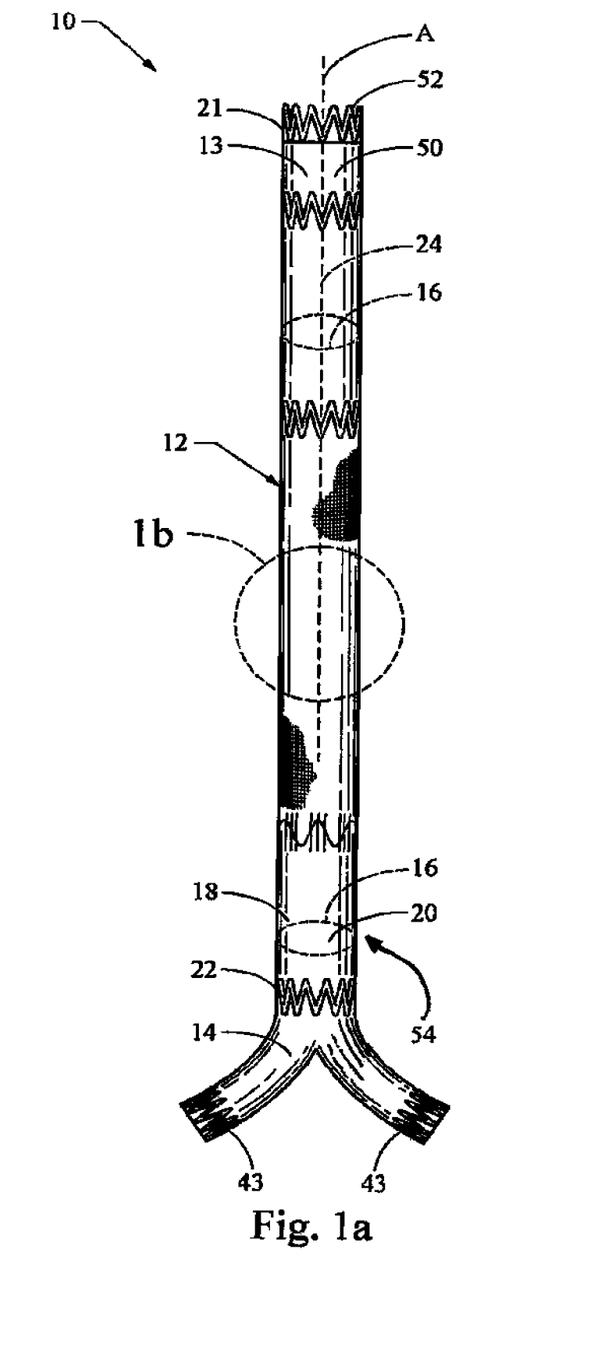
FIG. 1a is a side view of an implantable graft device having floating yarns in accordance with one embodiment of the present invention.

FIG. 1a illustrates an implantable graft device 10 having floating yarns in accordance with one embodiment of the present invention. As shown, the device 10 comprises a graft body 12, an anchor portion 13 extending proximally therefrom, and an end portion 14 extending distally from the graft body 12. As further shown, the graft body 12 preferably comprises an inner side 16 and an outer side 18. The inner side 16 of the graft body 12 forms a lumen 20 defining a longitudinal axis A and comprises proximal end 21 and distal end 22. In this embodiment, the graft body 12 may comprise any suitable yarn, e.g., elastic yarn, polyester yarn, or a combination thereof.

Figure 1B:
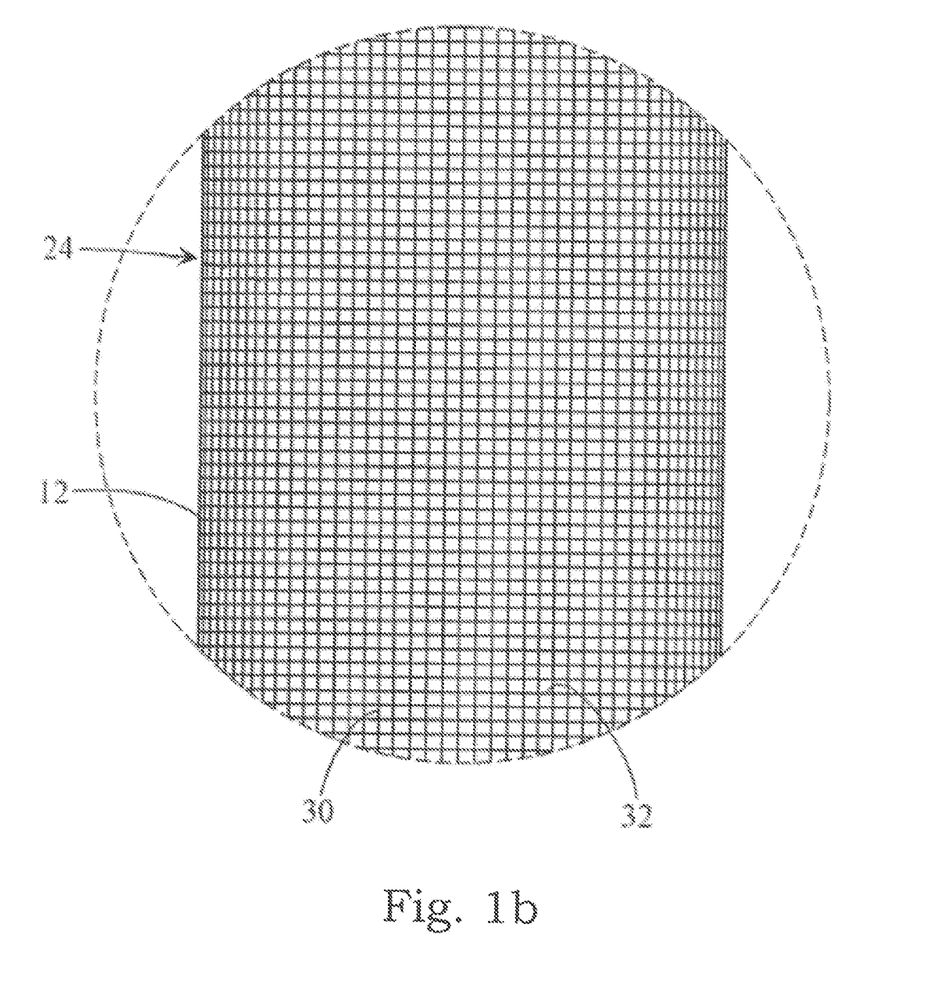

As shown in FIG. 1b, the graft body 12 comprises a woven fabric 24 having warp yarns 30 aligned in a first direction and weft yarns 32 aligned in a second direction. In this example, the first direction is perpendicular to the second direction. Preferably, the warp yarns 30 are the lengthwise threads attached to a loom before weaving begins. The weft yarns 32 (also known as woof or fill yarns) are the yarns that are shuttled back and forth across the warp yarns 30, defining the woven fabric 24. Each of the warp and weft yarns 32 may be a thread of spun fibre. The fibre may be comprised of a various material (discussed in greater detail below). In one embodiment, the elastic yarns may be the weft yarn and polyester yarns may be the warp yarns 30. The yarns may also be made of polyester, polypropylene, polyethylene, polyurethane, and polytetrafluoroethylene. Moreover, each yarn may take on any suitable cross-sectional shape, e.g., round, obround, polygonal, rectangular, square, or free form, or combinations thereof. Furthermore, the graft body 12 may comprise between about 10 and 1000 weft yarns per inch, preferably between about 50 and 300 weft yarns per inch. The graft body may comprise between about 10 and 1000 warp yarns per inch, preferably between about 10 and 200 warp yarns per inch.

Figure 1C:
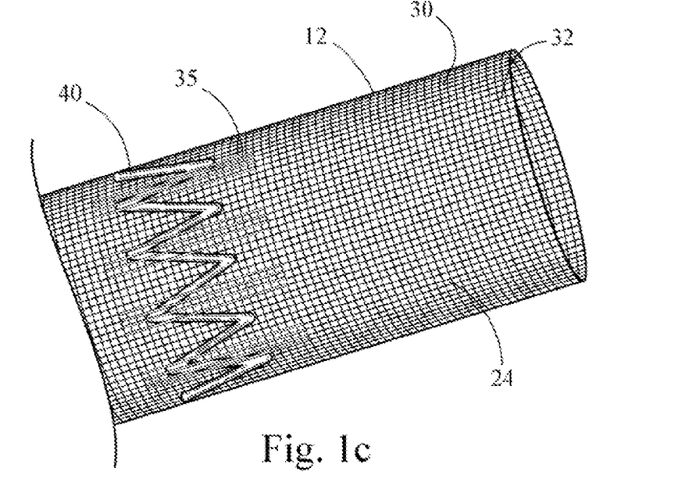

As shown in FIGS. 1a and 1c, the graft body 12 has weft yarns 32 and warp yarns 30 interwoven together defining the woven fabric 24. In one embodiment, a portion of warp yarns 30 along the longitudinal axis A are not interwoven with some of the weft yarns 32. Preferably, the portion of warp yarns 30 are not woven with some weft yarns 32 at a predetermined location or area along the longitudinal axis A. For example, plain weaving of the portion of warp yarns 30 may be skipped at the predetermined location or area. This creates "floating" or non-woven yarns having "loops" 35 aligned generally in the first direction.

Figure 1D:
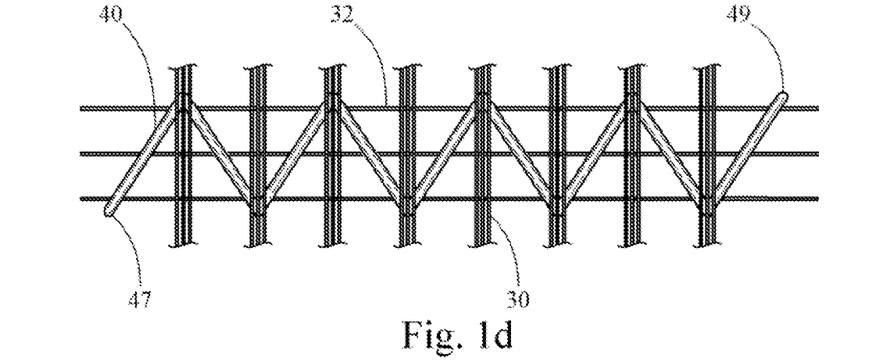
Figure 1E:
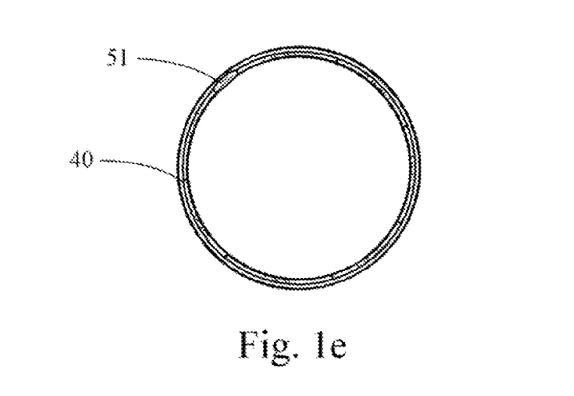
FIG. 1e is an end view of the stent of FIG. 1d when first and second ends are attached.

FIGS. 1c and 1d depict an expandable stent 40 disposed about the graft body along the longitudinal axis. As shown, a planar wire 40 has a first end 47 and a second end 49 before attachment of the first and second ends 47, 49, defining the expandable stent 40. In this embodiment, the first end is inserted through the loops 35 circumferentially about the graft body. When the wire is disposed about the graft body, the first and second ends are attached by any suitable means 51 such as by soldering or adhesive as shown in FIG. 1e.

In another embodiment, a portion of warp yarns and some of the weft yarns are not interwoven with weft yarns and warp yarns, respectively. At predetermined locations or areas, the portion of warp yarns are not woven with weft yarns along the longitudinal axis A and some of the weft yarn are not woven with warp yarns. For example, plain weaving of the portion of warp yarns may be skipped at a predetermined location or area along the longitudinal axis. This creates floating or non-woven yarns having loops aligned generally in both the first and second directions.

Figure 2:
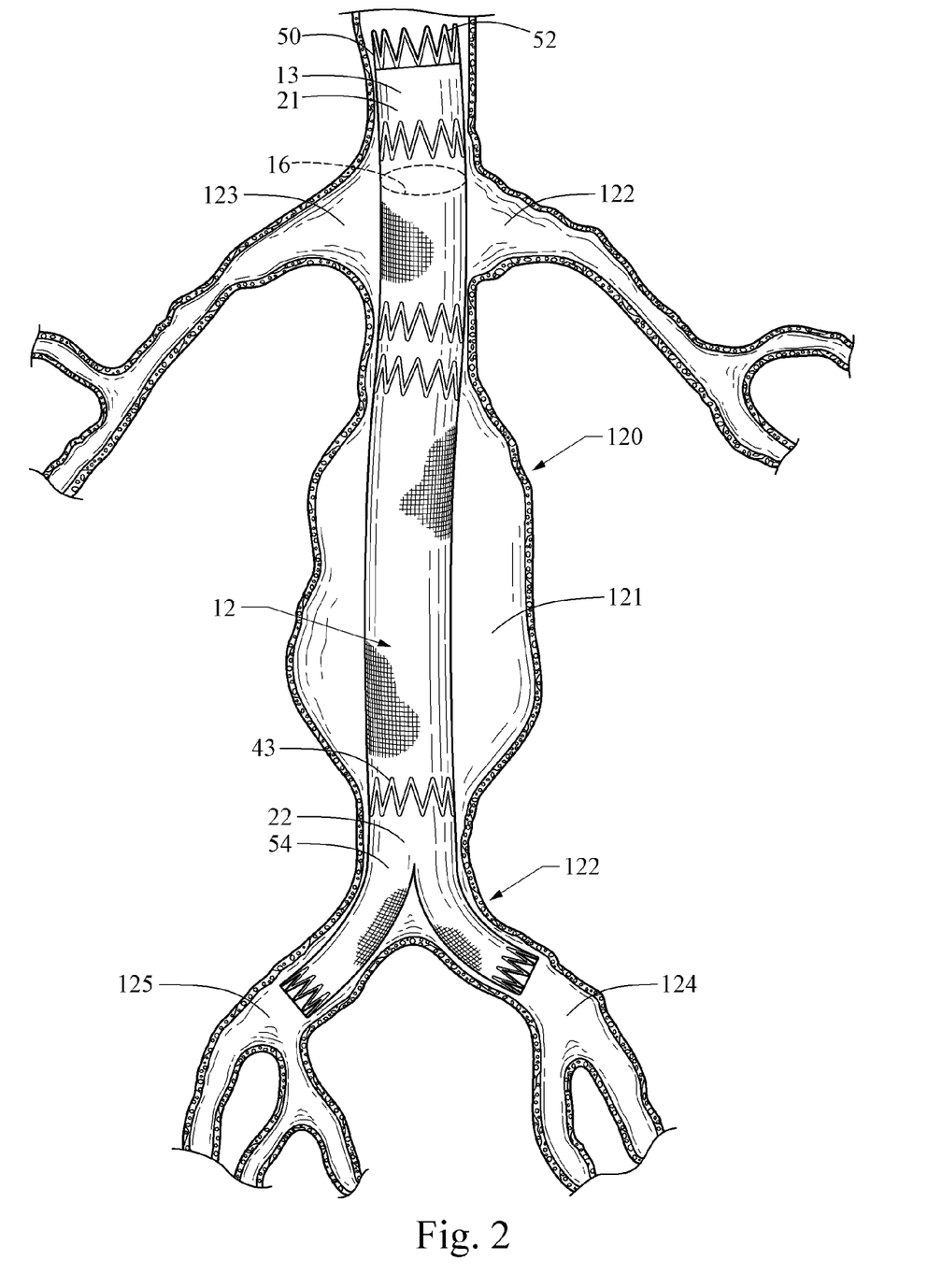

As further shown in FIGS. 1a to 2, the anchor portion 13 extends from the proximal end 21 of the graft body 12. Preferably, the anchor portion 13 has a first woven portion 50 and a barb stent 52 attached thereto for reduced migration of the graft device 10. In this embodiment, the first woven portion 50 is comprised of woven yarn. As shown, the first woven portion 50 comprises an inner side 16 to which the barb stent 52 is attached by any suitable means. In this embodiment, the barb stent 52 comprises a plurality of loops that are configured to be attached by sewing to the inner side 16 of the first woven portion 50.

In this embodiment, the end portion 14 extends from the distal end 22 of the graft body 12. As shown, the end portion 14 has a second woven portion 56 and a stent attached thereto. Preferably, the expandable stent 43 is attached to the inner side 16 of the graft device 10. The second woven portion 56 is also preferably comprised of woven yarn.

FIG. 2 illustrates the aortic stent graft device 10 implanted within the renal arteries 122, 123 and the iliac arteries 124, 125 in accordance with one embodiment of the present invention. The aorta 120 has an aneurysm 121 between the renal arteries 122, 123 and the iliac arteries 124, 125. Though the above embodiments illustrate grafts located within the aorta, prostheses of the present invention may be implanted in any body vessel, including main vessels in which one or more branch vessels may be located.

Figure 3:
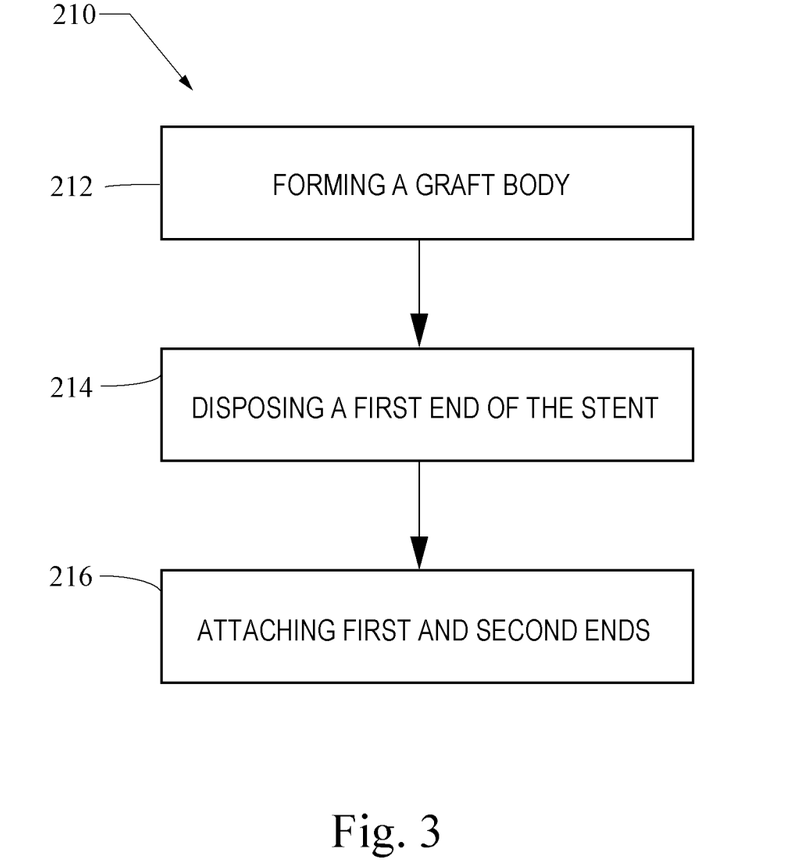
FIG. 3 is a flow chart of one method for making an implantable graft device having floating yarns in accordance with another example of the present invention.
Figure 4A:
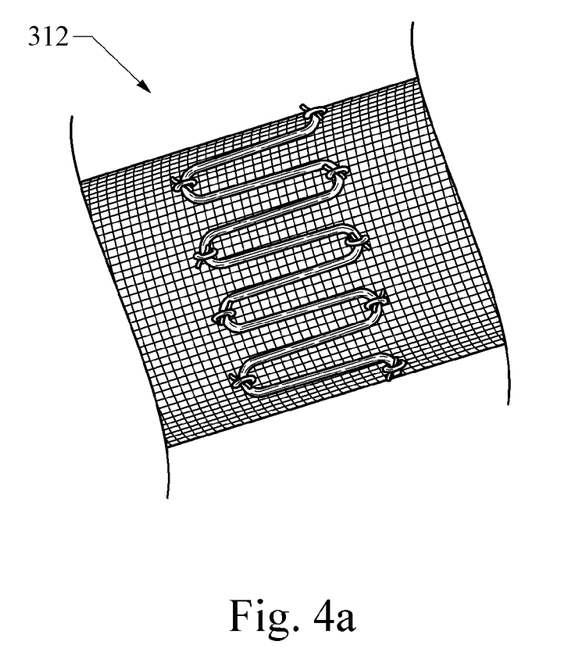
FIGS. 4a-4d are enlarged views of implantable stent graft in accordance with other embodiments of the present invention.
Figure 4B:
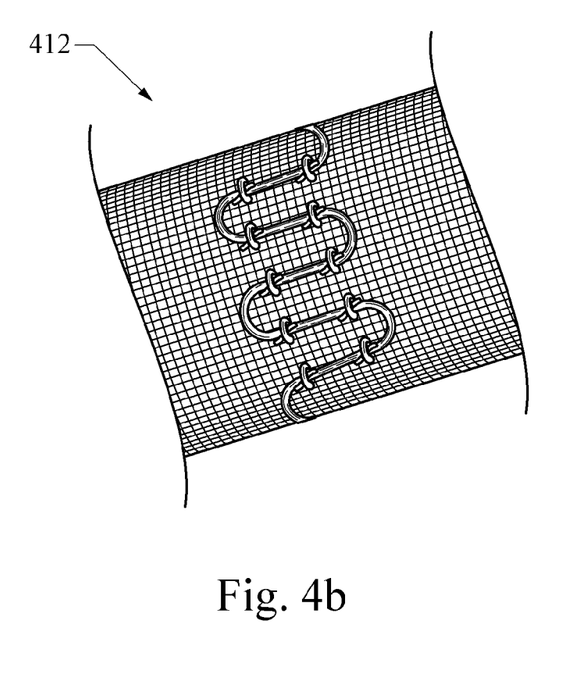
Figure 4C:
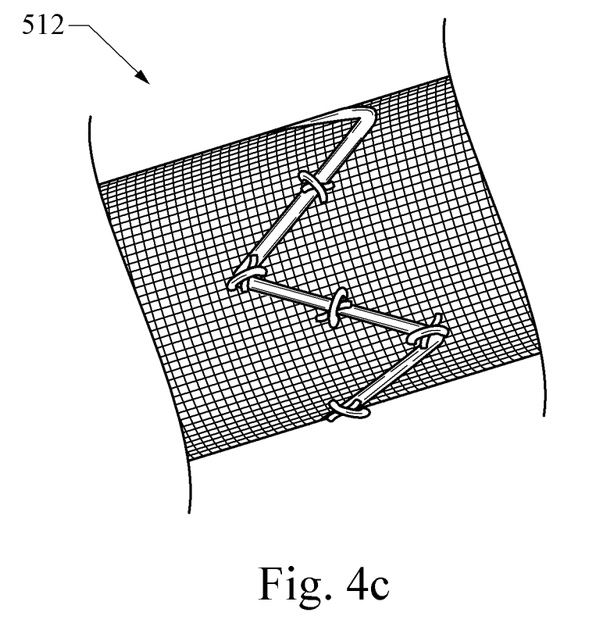
Figure 4D:
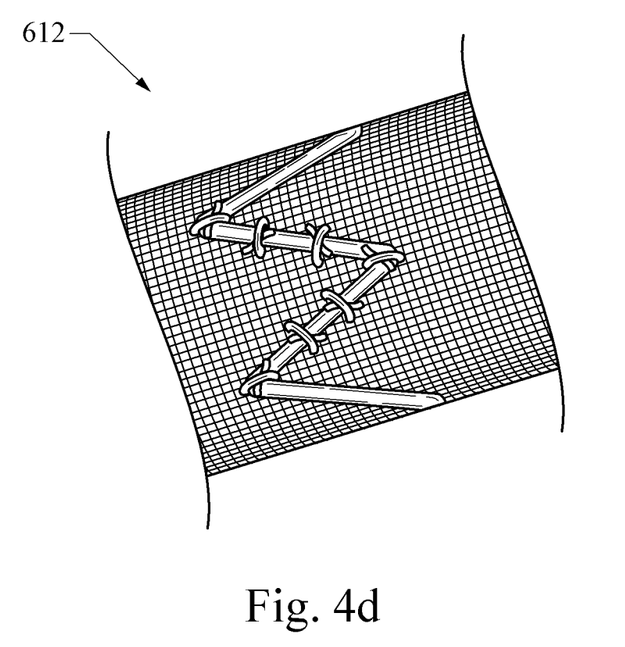

FIG. 3 is a flow chart depicting a method 210 for making the implantable graft device 10 having floating yarns in accordance with one example of the present invention. In this example, the method 210 comprises forming in box 212 the graft body 12 (discussed above). As mentioned, the graft body is formed with a lumen 20 to define a longitudinal axis. In this example, the graft body 12 has proximal end 21 and distal end 22 defining a woven fabric 24 having warp yarns 30 aligned in a first direction and weft yarns 32 aligned in a second direction and inner woven with the warp yarns 30. A portion of the warp yarns are not woven with some weft yarns at a predetermined location or area, defining floating yarns having loops.

As shown, the method 210 further comprises in box 214 disposing a first end of the stent circumferentially about the longitudinal axis and is received through the floating yarns to attach the stent to the graft body. The first and second ends are attached in box 216 to close the stent about the graft body. As mentioned above, this may be accomplished by any suitable means, e.g., welding or adhesive.

The anchor portion 13 may be attached to the proximal end 21 and extend therefrom. As shown, the anchor portion 13 has a first woven portion 50 comprised of woven yarn. Preferably, the reduced diameter yarn of the graft body 12 has a smaller diameter than the yarn of the first woven portion 50. As in FIG. 1, the first woven portion 50 has a barb stent 52 attached thereto for reduced migration of the graft device 10. The end portion 14 may be attached to the distal end 22 by any suitable means, i.e., sewing or stitching, and extends therefrom. As shown, the end portion 14 has a second woven portion 56 and an expandable stent 43 attached thereto. The second woven portion 56 is comprised of woven yarn.

FIGS. 4a-4d illustrate partial views of graft bodies 312, 412, 512, 612 of a stent graft device in accordance with other embodiments of the present invention. As shown, some of the warp yarns are not woven with weft yarns at various predetermined locations or areas along the graft body in general alignment the longitudinal axis. In one example, pairs of loops are attached together at the apices of each. In another example, pairs of loops are attached together at one apex of one loop and one side of the other loop. In yet another example, pairs of loops may be attached together at the sides of each. Combinations of attachments may vary based on location on the graft body and use without falling beyond the scope or spirit of the present invention.

Graft Material

The graft material may comprise any biocompatible material suitable for weaving. The graft material may be natural, synthetic, or manufactured. For example, biocompatible materials include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a graft body, provided the final textile is biocompatible.

Polymeric materials suitable for weaving graft material include polyethylene, polypropylene, polyaramids, polyacrylonitrile, nylons and cellulose, in addition to polyesters, fluorinated polymers, and polyurethanes as listed above. Desirably, the graft body material comprises one or more polymers that do not require treatment or modification to be biocompatible. More desirably, the graft body material comprises biocompatible polyesters. Even more desirable, graft body material comprises polyethylene terephthalate and PTFE. A preferred commercial example of polyethylene terephthalate especially suitable for weaving is Dacron™. These materials are relatively inexpensive, easy to handle, have good physical characterstics and are suitable for clinical application.

The graft material may be woven of a single material or combination of materials. Determination of which combination of materials woven in which direction of the graft body that is most appropriate may be based on the type of clinical application, properties of the graft body that are desired, and further factors such as the weave type, yarn properties such as the size or denier of the yarn, finishing techniques, and/or permeability of the textile. For example, for percutaneous application, thin graft body are preferred. Such thin grafts comprise yarns that have are fine or have a low denier. Desirably, graft body yarns range in size from about 0.1 denier to about 200 denier.

Graft Weaves

The graft may comprise any kind of suitable weave or weaves. For example, the graft body may include, but is not limited to, weaves such as plain weaves, modified plain weaves, basket weaves, rep or rib weaves, twill weaves (e.g., straight twill, reverse twill, herringbone twill), modified twill weaves, satin weaves, double weaves (e.g., double-width, tubular double weave, reversed double weave), and any other related weaves. In one embodiment, the graft body comprises a plain weave having 150 ends per inch and 250 picks per inch. An "end" refers to an individual warp yarn, and "sett" is the number of warp yarns per inch in a woven fabric. A "pick" refers to an individual weft yarn, and "pick count" is the number of weft yarns per inch in a woven fabric.

Stents

One or more stents may be attached or adhered to the graft body by any means known to one skilled in the art, including but not limited to welding, stitching, bonding, and adhesives. In one preferred embodiment, stents may be sutured to the graft body. In general, stents for use in accordance with the present invention typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

In one embodiment, stents are located distal and proximal to the graft body. For example, as shown in FIG. 1, stent 36 is located on the proximal end of the graft body 12 and stent 54 is disposed at the distal end. Stents located distally and proximally to a graft body provide structure and rigidity to the graft body. Additionally, proximal and distal stents may seal against the main vessel wall to prevent leakage around a branch vessel following perforation.

As shown in FIG. 2, stents are located at the proximal and distal ends of the graft body. Stents may seal against the main vessel wall 122 to prevent undesirable fluid leakage, for example by reducing blood leakage into an aneurysmal sac 121 spanned by an implanted graft body. Additional stents may further aid in sealing against the vessel wall 122 to prevent undesirable fluid leakage into the aneurysmal sac 121.

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any blood vessel including coronary arteries and peripheral arteries (e.g., renal, superficial femoral, carotid, and the like), a urethral stent, a biliary stent, a tracheal stent, a gastrointestinal stent, or an esophageal stent, for example. Desirably, the stent is a vascular stent such as the commercially available Gianturco-Roubin FLEX-STENT®, GRII™, SUPRA-G, or V FLEX coronary stents from Cook Incorporated (Bloomington, Ind.).

The stents may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Radiopacity

The graft body may be marked for radiographic visualization to facilitate precise alignment within the aortic artery with the particular branch anatomical conduit (e.g., carotid, innominate, subclavian, intercostal, superior mesenteric, celiac, renal, iliac, hypogastric, or visceral vessels). Radiopaque portions of the graft body would be seen by remote imaging methods including X-ray, ultrasound, Magnetic Resonance Imaging and the like, or by detecting a signal from or corresponding to the marker.

In other embodiments, the delivery device can comprise indicia relating to the orientation of the frame within the body vessel. In other embodiments, indicia can be located, for example, on a portion of a delivery catheter that can be correlated to the location of the prosthesis within a body vessel.

Radiopaque materials may be added to the graft body by any fabrication method or absorbed into or sprayed onto the surface of part or all of the graft. The degree of radiopacity contrast can be altered by implant content. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Attachment of Graft Device in Body Vessel

Prostheses according to the present invention may optionally include supplemental attachment means such as anchoring members, suturing, stapling, searing, bonding, gluing, bioadhesives, or otherwise adhering the medical device to the vessel wall or combinations thereof. For example, the graft body may be secured in place with one or more anchoring devices.

The art provides a wide variety of structural features that are acceptable for use in medical devices as anchoring members, and any suitable structural feature can be used. For example, individual barbs may be used to implant the graft body into a body vessel. The barbs may be secured to the graft body by any means known to one skilled in the art, including but not limited to welding to included stents, stitching, bonding, and adhesives. Desirably, barbs may be attached to stents included in the prosthesis. In some embodiments, the number, arrangement, and configuration of barbs can vary according to design preference and the clinical use of the graft body. The barbs can have any suitable shape, including points or "fish hook"-like configurations. The barbs may or may not penetrate the vessel wall, depending on their design and other factors.

Alternatively or in addition to anchoring members, bioadhesives may be used for attachment. Bioadhesive may be included in any suitable part of the prosthesis. Preferably, the bioadhesive is attached to the abluminal surface of the graft body. Selection of the type of bioadhesive, the portions of the prosthesis comprising the bioadhesive, and the manner of attaching the bioadhesive to the prosthesis can be chosen to perform a desired function upon implantation. For example, the bioadhesive can be selected to promote increased affinity of the desired portion of prosthesis to the section of the body vessel against which it is urged.

Bioadhesives for use in conjunction with the present invention include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta (TGF-B); (4) polysaccharides such as acacia, carboxymethyl-cellulose, dextran, hyaluronic acid, hydroxypropylcellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivatized with sticky molecules such as arginine, glycine, and aspartic acid, and copolymers.

Furthermore, commercially available bioadhesives that may be used in the present invention include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the graft body can include at least one bioactive agent. The bioactive agent can be included in any suitable part of the prosthesis. The bioactive materials can be attached to the prosthesis in any suitable manner. For example, a bioactive agent may be sprayed onto the graft body material, or stents may be dipped in bioactive agent. Selection of the type of bioactive agent, the portions of the prosthesis comprising the bioactive agent, and the manner of attaching the bioactive agent to the prosthesis can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive agent can be selected to perform one or more desired biological functions. For example, the abluminal surface of the graft body can comprise a bioactive selected to promote the ingrowth of tissue from the interior wall of a body vessel, such as a growth factor. An anti-angiogenic or antineoplastic bioactive such as paclitaxel, sirolimus, or a rapamycin analog, or a metalloproteinase inhibitor such as batimastat can be incorporated in or coated on the prosthesis to mitigate or prevent undesired conditions in the vessel wall, such as restenosis. Many other types of bioactive agents can be incorporated in the prosthesis.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Delivery of Graft Device

The graft device can be configured for delivery to a body vessel. For example, a prosthesis comprising a graft body and stents according to the present invention can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present invention can be adapted for deployment using conventional methods known in the art and employing percutaneous transluminal catheter devices. The prostheses are designed for deployment by any of a variety of in situ expansion means.

In one embodiment, a prosthesis comprising self-expanding stents and a graft body of the present invention may be mounted onto a catheter that holds the prosthesis as it is delivered through the body lumen and then releases the prosthesis and allows it to self-expand into contact with the body lumen. This deployment is effected after the prosthesis has been introduced percutaneously, transported transluminally and positioned at a desired location by means of the catheter. The self-expanding prosthesis may be deployed according to well-known deployment techniques for self-expanding medical devices. For example, the prosthesis may be positioned at the distal end of a catheter with a removable sheath or sleeve placed over the prosthetic valve to hold the prosthesis in a contracted state with a relatively small diameter. The prosthesis may then be implanted at the point of treatment by advancing the catheter over a guide wire to the location of the lesion, aligning graft body within the aortic artery and with any branch vessels, and then withdrawing the sleeve from over the prosthesis. The stent graft will automatically expand and exert pressure on the wall of the blood vessel at the site of treatment. The catheter, sleeve, and guide wire may then be removed from the patient.

In some embodiments, a bioabsorbable suture or sheath can be used to maintain a self-expanding stent graft in a compressed configuration both prior to and after deployment. As the bioabsorbable sheath or suture is degraded by the body after deployment, the prosthesis can expand within the body vessel. In some embodiments, a portion of the prosthesis can be restrained with a bioabsorbable material and another portion allowed to expand immediately upon implantation. For example, a self-expanding stent graft can be partially restrained by a bioabsorbable material upon deployment and later expand as the bioabsorbable material is absorbed.

In another embodiment, a stent graft may be first positioned to surround a portion of an inflatable balloon catheter. The prosthesis, with the balloon catheter inside is configured at a first, collapsed diameter. The prosthesis and the inflatable balloon are percutaneously introduced into a body vessel, following a previously positioned guide wire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthesis are positioned within the body passageway at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated, and the catheter may be withdrawn, leaving the prosthesis in place. The prosthesis may be covered by a removable sheath during delivery to protect both the prosthesis and the vessels.

While the present invention has been described in terms of preferred embodiments, it will be understood, of course, that the invention is not limited thereto since modifications may be made to those skilled in the art, particularly in light of the foregoing teachings.

The invention claimed is:

1. An implantable graft device comprising:
   a graft body forming a lumen defining a longitudinal axis and comprising proximal and distal ends, the graft body comprising a woven fabric having warp yarns aligned in a first direction and weft yarns aligned in a second direction, the weft yarns being interwoven with the warp yarns to form a weave pattern, a portion of the warp yarns along the longitudinal axis of the graft body not being interwoven with the weft yarns such that the portion of the warp yarns defines loops floating over the weft yarns and aligned in the first direction, each loop being a variation in the weave pattern; and
   an expandable stent disposed circumferentially about the longitudinal axis and received through each of the loops to attach the stent to the graft body.

2. The device of claim 1 wherein the first direction is perpendicular to the second direction.

3. The device of claim 1 wherein the expandable stent is comprised of one of stainless steel, nitinol, conichrome.

4. The device of claim 1 wherein the warp and weft yarns comprise a polymer.

5. The device of claim 4 wherein the polymer is selected from the group consisting of polyester, polypropylene, polyethylene, polyurethane, and polytetrafluoroethylene.

6. The device of claim 4 wherein the polymer comprises polyester.

7. The device of claim 5 wherein the body portion comprises between about 50 and about 300 weft yarns per inch and between about 10 and about 200 warp yarns per inch.

8. An implantable graft device comprising:
   a graft body forming a lumen defining a longitudinal axis and comprising proximal and distal ends, the graft body comprising a woven fabric having warp yarns aligned in a first direction and weft yarns aligned in a second direction, the weft yarns being interwoven with the warp yarns to form a weave pattern, a portion of the warp yarns along the longitudinal axis of the graft body not being interwoven with the weft yarns such that the portion of the warp yarns defines loops floating over the weft yarns and aligned in the first direction, each loop being a variation the weave pattern;
   an expandable stent disposed circumferentially about the longitudinal axis and received through each of the loops to attach the stent to the graft body;
   an anchor portion extending from the proximal end of the graft body, the anchor portion having a first woven portion and a barb stent attached thereto for reduced migration of the graft device, the first woven portion being comprised of woven yarn; and
   an end portion extending from the distal end of the graft body, the end portion having a second woven portion and a stent attached thereto, the second woven portion being comprised of woven yarn.

9. A method for making an implantable graft device, the method comprising:
   forming a graft body having a lumen defining a longitudinal axis and comprising proximal and distal ends, providing a woven fabric having warp yarns aligned in a first direction and weft yarns aligned in a second direction and interwoven with the warp yarns to form a weave pattern, a portion of the graft body having weft yarns that are not interwoven with the warp yarns such that a portion of the warp yarns defines loops floating over the weft yarns and aligned in the first direction circumferentially about the longitudinal axis, each loop being a variation in the weave pattern;
   subsequently disposing a first end of an expandable stent circumferentially about the longitudinal axis of the graft body and through the loops to attach the stent to the graft body; and
   subsequently attaching a second end of the stent to the first end to close the stent about the graft body.

10. The method of claim 9 wherein the first direction is perpendicular to the second direction.

11. The method of claim 9 wherein the expandable stent is comprised of one of stainless steel, nitinol, conichrome.

12. The method of claim 9 wherein the warp and weft yarns comprise a polymer.

13. The method of claim 12 wherein the polymer is selected from the group consisting of polyester, polypropylene, polyethylene, polyurethane, and polytetrafluoroethylene.

14. The method of claim 12 wherein the polymer comprises polyester.

15. The method of claim 14 wherein the body portion comprises between about 50 and about 300 weft yarns per inch and between about 200 and about 10 warp yarns per inch.

16. The method of claim 15 wherein the first direction is perpendicular to the second direction.

17. The method of claim 9 wherein attaching includes soldering, or adhesive bonding.

* * * * *